United States Patent [19]

Woo

[11] 4,170,141
[45] Oct. 9, 1979

[54] METHOD AND APPARATUS FOR MEASURING THE LOSS MODULUS OF MATERIALS

[75] Inventor: Lecon Woo, Wilmington, Del.

[73] Assignee: E. I. Du Pont de Nemours and Company, Wilmington, Del.

[21] Appl. No.: 880,944

[22] Filed: Feb. 24, 1978

[51] Int. Cl.² ............................................. G01N 3/38
[52] U.S. Cl. ....................................... 73/579; 73/812
[58] Field of Search .................... 73/579, 91, 100, 101, 73/808, 812, 815

[56] References Cited

U.S. PATENT DOCUMENTS

| | | | |
|---|---|---|---|
| 3,501,952 | 3/1970 | Gergen et al. | 73/15.6 |
| 3,508,437 | 4/1970 | Van Beek | 73/579 |
| 3,751,977 | 8/1973 | Schilling, Jr. | 73/101 |
| 4,034,602 | 7/1977 | Woo et al. | 73/579 |
| 4,049,997 | 9/1977 | McGhee | 318/128 |

Primary Examiner—Jerry W. Myracle

[57] ABSTRACT

The loss modulus of a material is ascertained by subjecting a sample of the material to a mechanical vibration at the resonant frequency of the material. The dynamic driving force required to maintain the material in mechanical vibration at its resonant frequency is measured. Next, the static driving force required to displace the same material the same distance as when vibrating is measured. The quotient of the dynamic force divided by the static force is proportional to the tangent of the angle between elastic modulus and loss modulus of the material, or tan δ. Since the frequency of the material, when in vibration, is related to the elastic modulus of material, the loss modulus may be readily computed by multiplying the elastic modulus by tan δ.

An apparatus capable of performing this method includes a driving system that vibrates the sample material at its resonant frequency using a sinusoidal driving force which is 90° out of phase with the material displacement and hence in phase with the sample's loss function.

5 Claims, 2 Drawing Figures

METHOD AND APPARATUS FOR MEASURING THE LOSS MODULUS OF MATERIALS

TECHNICAL FIELD

This invention relates to effecting quantitative damping measurements of materials and, more particularly, to a method and apparatus for measuring the loss modulus of materials.

BACKGROUND OF THE INVENTION

For many materials, including practically every manmade synthetic material, the mechanical behavior during processing as well as end product conditions is an important parameter that must be tightly specified and controlled. During the initial phases in the development of a new polymer or process, an understanding of the relationship between chemical structure and the physical properties of the process is of vital concern. Later on, in the process and quality control stages, factors such as mechanical strength, dimensional and thermal stability, and impact resistance are of utmost importance.

Virtually all synthetic materials in existence are viscoelastic, i.e., their behavior under mechanical stress lies somewhere between that of a purely viscous liquid and that of a perfectly elastic spring. Few materials behave like a perfect spring or a pure liquid. Rather, the mechanical behavior of these materials is generally time and/or temperature dependent and has led to such tests as creep, stress relaxation, tear, impact resistance, etc. One of the more important properties of materials sought is the materials' behavior under dynamic conditions. To explore this, a material's response to a cyclical stress as a function of temperature, time or frequency is determined. If a sample of a viscoelastic solid, for example, is deformed and then released, a portion of the stored deformation energy will be returned at a rate which is a fundamental property of the material. That is, the sample goes into damped oscillation. A portion of the deformation energy is dissipated in other forms. The greater the dissipation, the faster the oscillation dies away. If the dissipated energy is restored, the sample will vibrate at its natural (resonant) frequency. The resonant frequency is related to the modulus (stiffness) of the sample. Energy dissipation relates to such properties as impact resistance, brittleness, noise abatement, etc.

Because of their viscoelastic nature, the stress and strain in viscoelastic materials are not in phase, and, in fact, exhibit hysteresis. If a plot is made of this relationship, the area enclosed by the plot corresponds to the energy dissipated during each cycle of deformation of the material. In order to accurately describe this phenomenon, a complex modulus $E = E' + jE''$ is often used to characterize the material where E is Young's modulus, $E'$ is the real part and $E''$ is the imaginary part. The real part $E'$ of the modulus corresponds to the amount of energy that is stored in the strain and can be related to the spring constant, the complex part $E''$ corresponds to the energy dissipation or loss and can be related to the damping coefficient used in second order differential equations to define vibrating systems.

Many mechanical analyzers have been developed for testing and ascertaining such properties as the loss modulus and elastic modulus of materials and the variations of these properties as a function of both time and temperature. Among these systems are those described for example in U.S. Pat. Nos. 3,501,952 issued Mar. 24, 1970 to Gergens et al.; 3,508,437 issued Apr. 27, 1970 to Van Beek; 3,751,977 issued Aug. 14, 1973 to Schilling; 4,034,602 issued July 12, 1977 to Woo et al. and 4,049,997 issued Sept. 20, 1977 to McGhee. All of these systems place the sample under test into vibration or oscillation utilizing mechanical systems. These mechanical systems vibrate at a resonant frequency determined primarily by the sample. A drive transducer is used to maintain the system in oscillation, a displacement transducer is used to sense the displacement of the mechanical system, and a drive amplifier is used to energize the drive transducer sufficiently to maintain the system oscillating at resonance at a constant amplitude.

While many of these systems attempt to measure the elastic modulus ($E'$), the loss modulus ($E''$) is typically measured only on a relative basis by sensing the power input to the system that is required to maintain a constant oscillation amplitude. Unfortunately this does not provide a calibrated result in commonly accepted units. Other methods of determining the loss modulus are by obtaining the logarithmic decrement by free decay of the system. Unfortunately, this requires substantial additional instrumentation. Another method of determining loss modulus is to use the second order relationship that exists between oscillation frequency and amplitude. This approach, while satisfactory, does not always provide the results of the quality that might be desired.

Accordingly it is an object of this invention to overcome many of the disadvantages of the prior art methods for obtaining the loss modulus of materials.

Another object of this invention is to provide an improved method of obtaining the loss modulus of materials.

A further object of this invention is to provide an improved apparatus for ascertaining the loss modulus of materials.

DISCLOSURE OF THE INVENTION

According to the method of this invention, the loss modulus of a material is obtained using a mechanical system for subjecting the material to a vibratory mechanical displacement. The method includes the steps of periodically displacing the material at its resonant frequency, displacing the material a finite amplitude with a periodic driving force that varies sinusoidally and leads the actual displacement by about $\pi/2$ radians, displacing the material said finite amplitude using a static driving force, thereby to deform the material to the same extent as with said periodic driving force, and dividing the periodic driving force by said static driving force to obtain the tangent of the loss angle $\delta$ for said material from which the loss modulus may be computed.

By driving the material with driving forces which are directly related to the driving voltages, the quotient of the voltages may represent the tangent of the loss angle.

According to this invention, an apparatus for measuring the loss modulus of a material includes a dynamic mechanical apparatus for vibrating the material at its resonant frequency. The system includes a displacement transducer for providing an alternating signal corresponding to the instantaneous displacement of the mechanical system, a drive transducer for imparting mechanical displacement to the system, and feedback means responsive to the displacement signal for actuating the drive transducer to maintain the mechanical system oscillating at the resonant frequency of said material and at a constant amplitude. The drive means includes analog means for developing an analog signal related in amplitude to the power required to maintain the amplitude constant, switching means responsive to the zero crossover times of the alternating displacement signal for selectively actuating the drive transducer with the analog signal to maintain the resonant frequency, and means for selectively actuating the drive transducer with a sinusoidal signal whose peak value is related in amplitude to the analog signal, whereby the loss function of material, which is in phase with the sinusoidal signal, can be ascertained.

With such a system, the simple measurement of the ratio of forces applied to the system under both dynamic and static conditions is equal to tangent of the loss angle $\delta$ which is equal to $E''/E'$. Since the elastic modulus $E'$ may be measured by many approaches it is a simple matter now to compute $E''$, the loss modulus. A particular advantage of this system is that the static deflection need be measured only once for a particular material and no force calibration of the drive system is necessary. The determination of the absolute value of tan $\delta$ is reduced simply to the ratio to voltages, namely the driving voltages of the apparatus necessary to maintain the respective dynamic and static deflections.

BEST MODE FOR CARRYING OUT THE INVENTION

Figure 1:
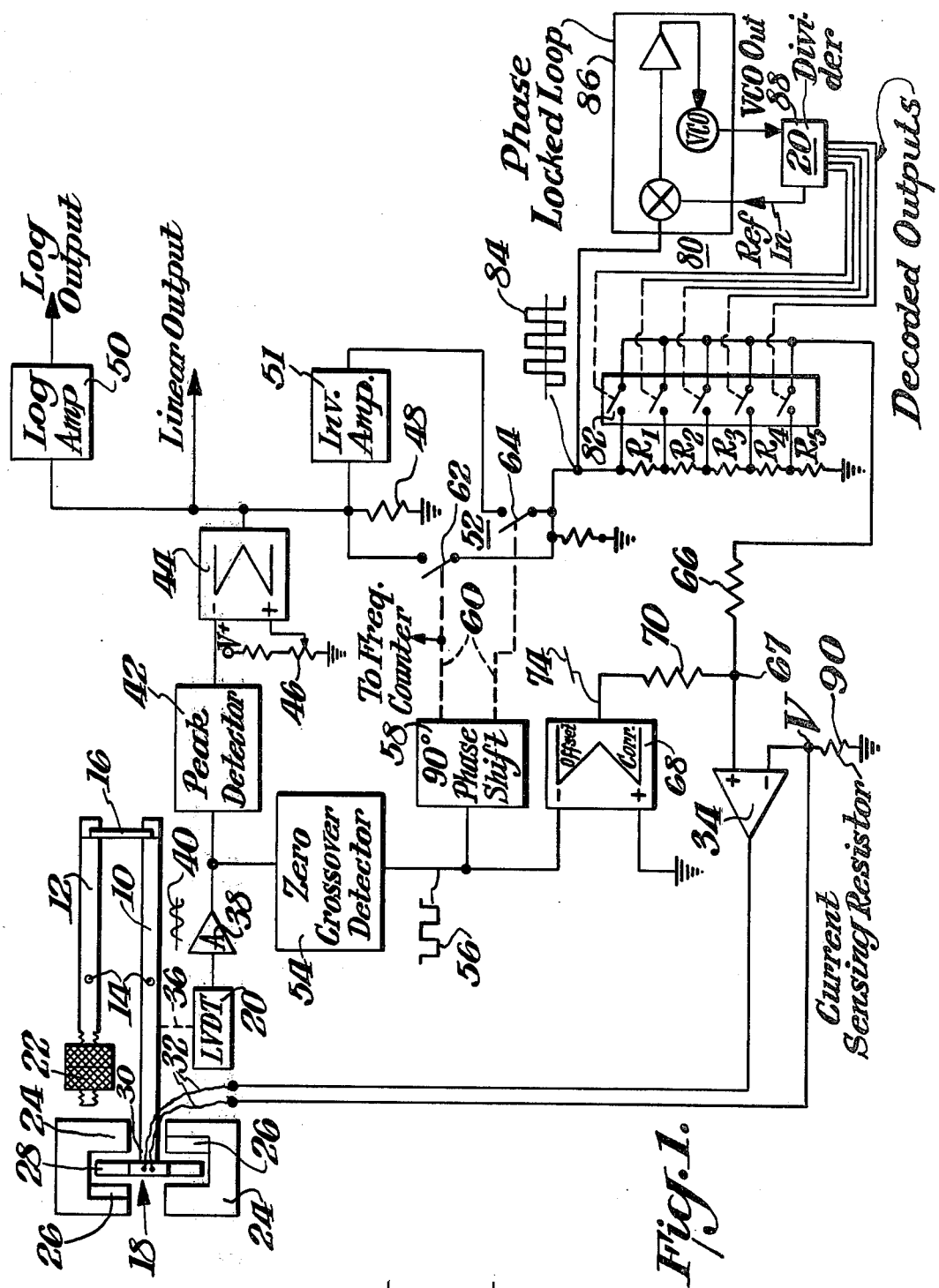
FIG. 1 is a block diagram of a drive system for a dynamic mechanical analyzer constructed in accordance with this invention.

There is described in the Woo et al. U.S. Pat. No. 4,034,602, assigned to the same assignee as this application, a dynamic mechanical analyzer for testing materials. As is described by Woo et al., such analyzer may be used to measure the complex modulus E and other physical properties of materials. This measurement is made by subjecting a sample of the material under test to a well defined mechanical oscillatory motion which stresses the sample. The Woo et al. analyzer, depicted in FIG. 1, modified in accordance with this invention, incorporates two parallel sample arms 10, 12 (a driving arm 10 and a driven arm 12) each pivotally mounted at their central portion by pivots 14. If flexure pivots are used, they have precisely known, low spring constants. A sample 16 is clamped between one end of each of the arms 10, 12 such that the only coupling between the arms is the sample. An electromechanical driver 18 is positioned at the opposite end of the driving arm 10 together with a displacement transducer 20.

The remainder of the block diagram seen in FIG. 1 of the drawing constitutes a control arrangement for maintaining the in-phase oscillation of the arms 10 and 12 at a constant amplitude and at the resonant frequency of the system as determined primarily by the elastic modulus of the sample 16 and the spring constants of the flexure pivots 14, if flexure pivots are used. The driven arm 12 has a counter weight 22 which is used to balance the arm against the driving arm.

A linear drive system is employed and incorporates a pair of U-shaped iron pole pieces 24, a permanent magnet such as a ferrite magnet 26 associated with each pole piece, and a pancake coil 28 disposed in the air gap provided by the pole pieces 24 and the magnets 26. The pancake coil 28 is a uniformly wound, flat coil secured to the driven end 30 of the driving arm 10. Lead wires 32 from the pancake coil are connected to a drive amplifier 34 which supplies the necessary current for causing the coil to move within the magnetic field (at right angles to the field) and thereby cause a vibratory or oscillatory motion of the driving arm 10 about the pivot 14, as will be described. The driven arm 12, coupled via the sample 16 to the driving arm oscillates substantially in-phase with the driving arm, the frequency and amplitude of the oscillation being primarily determined by the elastic modulus of the sample.

This mechanical motion of the arms 10 and 12 is sensed by a suitable displacement transducer 20 which may be any of those well known in the art. Preferably this transducer may be a linear voltage differential transformer of known type which is mechanically coupled as depicted by the dashed line 36 to one of the arms, in this case to the driving arm 10. As is known, a linear voltage differential transformer displacement transducer provides an output voltage signal which varies in amplitude and frequency in accordance with the movement of the arm 10 whose displacement is being sensed. This displacement signal is amplified by an amplifier 38 to provide an alternating waveform such as is depicted by the curve 40. The amplifier displacement signal 40 is passed to a peak detector 42 which provides a direct current output signal varying in amplitude in accordance with the peak amplitudes of the signal 40. This peak detected signal is coupled to the negative-going input of a gain control integrator 44 so that it may be compared with a predetermined reference level, such as is established by a potentiometer voltage divider 46, which is applied to the positive-going input of the same integrator. Thus the output of the integrator 44 will be a relatively constant voltage level or analog signal which is developed across an output resistor 48. By proper adjustment of the voltage divider 46, the analog signal developed across the output resistor 48 may be related to the power required in the system to maintain the amplitude of the mechanical vibrations or oscillations constant. Thus by time switching the analog signal and using the switched signal to drive the system, the amplitude of the oscillations of the arms is maintained constant. Also by amplifying it using any suitable type of logarithmic amplifier 40, the dynamic range of the output is enhanced. The analog signal developed across the output resistor 48 is coupled through a switching circuit 52 and a switched divider network 80 to the drive amplifier 34, which energizes the drive transducer 18 to maintain the mechanical system in oscillation.

The switching system 52 functions, as will be described, to maintain the signals applied to the drive amplifier 34 in-phase with the vibratory motion of the mechanical system. This is accomplished by a zero crossover detector 54, which is a high gain amplifier that shapes, due to its high gain, the signals into a rectangular waveform 56. Hereinafter such amplifiers will be referred to as squaring amplifiers. The vertical going components of the waveform 56 correspond in time to the zero crossover points of the displacement signal 40. This rectangular signal is sent through a 90° phase shifter 58, which may be of conventional design such as that described in said McGhee U.S. Pat. No. 4,049,997, to change the phase of this rectangular signal 56 such that the zero crossovers correspond in time to the peaks of the displacement signal 40. It is these phase shifter signals which are used to control the switching circuitry 52. This phase shift circuit 58 has outputs that are 180° out of phase depicted by the dashed lines 60, which may be relays but preferably are analog switches 62 and 64 respectively. These analog switches may be of a known type, such as integrated circuit chips MC 14016CP. To this end, the first switch 62 connects the analog voltage $V_1$ across the resistor 48 through the divider network 80, as will be described, and a summing resistor 66 to a summing point 67 which is the input of a drive amplifier 34. In like manner the voltage across the resistor 48 is coupled through an inverting amplifier 51 of conventional design, the second analog switch 64, the divider network 80, and the summing resistor 66 to the summing point 67. The output to the switching circuitry is a square wave depicted by the wave form 84.

There is provided an offset correction circuit which receives the rectangular waveform 56 and automatically adjusts the drive voltage of the mechanical system. This offset correcting circuit may include an integrating circuit 68 in which case the rectangular waveform 56 is applied to the negative-going input of the integrator and the positive-going input is referenced to ground. The output of this integrator is thus an offset signal whose level varies in accordance with the asymmetry of the signal derived from the displacement transducer 20. This asymmetry may be due to asymmetrical placement of the transducer itself, asymmetrical vibration due to a misaligned drive system, or misalignment in mounting the sample 16. In any event, any asymmetry in the system, as manifested in the displacement waveform, will be corrected by the integrator 68 by changing the level of the voltage of which is coupled through a summing resistor 70 to the summing point 67. The offset signal is a slowly varying DC level, depicted by the waveform 74, and is combined with the switched voltages from the analog signal developed across resistor 48 to control the operation of the drive transducer 18. The offset correction integrator 68 adjusts the displacement waveform 40 such that the crossover times are equally spaced; i.e., symmetrical in time.

In accordance with this invention, the square wave signals from the switches 52 are coupled through the switched divider network 80, which functions as a sine wave synthesizer circuit to convert the square waves into sinusoidal waves prior to application to the resistor 66. Five resistors R1, R2, R3, R4, and R5, which are selected in value to conform to various points between 0 and $\pi/2$ of a sinusoidal waveform are connected in series from the switches 52 to ground. Each resistor is bypassed by a switch 82, which may be an FET transistor. These switches 82 are triggered in sequence at a rate twenty times the frequency of the square wave 84 (the oscillatory system frequency). This switching frequency is obtained by coupling the square wave 84 also to a phase locked loop 86 whose VCO is coupled to a divider (by twenty) 88 which provides series of five output switching pulses on each of five output lines which drive the FET switches 82. The phase locked loop may be an RCA CD4046, the divider RCA CD4017 and CD4027, the FET switches RCA CD4016.

Figure 2:
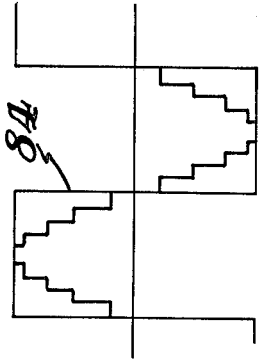
FIG. 2 is a plot, amplitude vs. time, of the manner in which the drive signal of FIG. 1 may be converted into sinusiodal form.

In this manner the square wave 84 is converted, by the switched sine wave (FIG. 2) approximated by twenty segments using only five resistors and five semiconductor devices. A further advantage is the integrity of the drive circuit permits the phase and amplitude information to be preserved. Since the drive is now a sine wave signal that is located 90° out of phase with the position or displacement signals 40, the sine wave drive signal depicted in FIG. 2 is in-phase with the sample's dissipation function. Also, since the current flowing through the coil is directly proportional to the input voltages applied to the drive amplifier, the force that is imparted to the sample-apparatus system equals KV, where K is a constant for given driver and is made up from contributions such as magnetic field intensity, number of turns in the coil and the like. The voltage V is the input voltage which may be measured directly using a current sensing resistor 90 tapped off the drive coil.

This apparatus facilitates performing the method of this invention. In a mechanically resonant system for testing samples, if the sample is driven by a sine wave at its resonant frequency and the drive amplitude is maintained at a fixed value, then tan $\delta$ of the system is the ratio between the peak dynamic driving force and the static driving force necessary to achieve the same displacement or deformation of the material. Since these forces are directly proportional to the input voltages then tan $\delta = F_1/F_0 = V_1/V_0$. In this way no force calibration for the drive system is necessary and the measurement of tan $\delta$ is reduced simply to the ratio of two voltages.

The derivation of the formula for this relationship may be seen as follows:

(A) By definition $$\tan \delta = \frac{E''}{E'} = \frac{G''}{G'} = \frac{1}{2\pi}\left(\frac{\Delta W}{W}\right) \quad (2)$$

where
$\Delta W$ = energy dissipation per cycle
$W$ = maximum energy in the system (potential or kinetic) now,
$W = \frac{1}{2}\mathcal{K}\epsilon^2$ — potential energy where $\mathcal{K}$
 = generalized modulus function, including form factors
$\epsilon$ = strain in the direction of applied force also, $$E_{input} = \int_0^T \delta W$$

Energy Input Per Cycle $\delta W$ = instantaneous work imparted by the driver to system = force function $\times$ velocity at the point of application $\times$ dt = $F_1$ sin $\omega t \times \delta_1 \times \omega \times$ Cos $(\omega t - \alpha)$dt where
$F_1$ = max. force amplitude
$\omega$ = angular frequency
$\alpha$ = phase shift between force and position therefore, $$E_{input} = \int_o^T F_1 \sin \omega t \times \epsilon_1 \times \omega \times \cos(\omega t - \alpha)dt \quad (3)$$
$= \frac{1}{2} \epsilon \omega F_1 \tau \sin \alpha$
$= \Delta W$, since via feedback, a stationary state is maintained Also under resonant condition,
$\alpha = \pi/2 \sin \alpha = 1$ therefore,
$$\Delta W = \pi \epsilon F_1$$

However, from Hooke's Law,
$$F_o = K\epsilon_0 \text{ or } W = \tfrac{1}{2}F_0\epsilon_0$$

therefore
$$\frac{\Delta W}{W} = \frac{\pi \epsilon_1 F_1}{\tfrac{1}{2} F_0 \epsilon_0}$$

if $\epsilon_1 = \epsilon_0$
$$\frac{\Delta W}{W} = 2 \frac{F_1}{F_0} = 2 \text{ Tan } \delta$$

or,
$$\text{Tan } \delta = F_1/F_0 \qquad (4)$$

but,
$$F_1 = KV_1$$
$$F_0 = KV_0$$

where
K = transducer constant
$V_0$ = static input voltage to amplifier
$V_1$ = peak dynamic input voltage to amplifier to achieve identical sample displacement therefore
$$\text{Tan } \delta = \frac{KV_1}{KV_0} = \frac{V_1}{V_0}$$

In the course of a test, $V_0$ need only be measured once, i.e., during a calibration step. $V_0$ at other frequencies ($f_2$) can be related to $V_0$ of the original frequency ($f_1$)

$$V_0(f_2)/V_0(f_1) = f_2^2/f_1^2$$

In fact, permanent calibration of $V_0$ can be obtained by using a predominantly elastic sample such as spring steel and measure its $V_0$ and frequency $f_3$ · a formula of the form $$\text{Tan } \delta (f_1) = K' \frac{V_1(f_1)}{f_1^2}$$

can be obtained.

Where K' is the permanent calibration constant of the instrument containing $V_0$, $f_3$ for steel and, or scale factors for resistor ratios for $R_{70}$ and $R_{66}$.

Using the systems of Woo et al. or McGhee or the apparatus of this invention permits the elastic modulus (E') to be calculated simply by measuring the resonant frequency of the system. A formula for effecting this computation is:

Modulus-Frequency Relationship $$E' = \frac{(4\pi^2 f^2 J - K)}{2W(\frac{L}{2} + D)^2} \left(\frac{L}{T}\right)^3$$

where
E = Young's modulus (N/m² = Pa)
f = DMA frequency (Hz)
J = Moment of inertia of arm (kg · m²) (1.6×10⁻³ kg m², nominal)
K = Spring constant of pivot (kg · m²/sec²) (0.33 kg m²/sec² Rad, nominal)
D = Clamping distance (9.52×10⁻³ m, nominal)
W = Sample width (m)
L = Sample length (m)
T = Sample thickness (m)

Hence from the relationship tan $\delta$ = E"/E', since tan $\delta$ and E' can be determined using the method and/or apparatus of this invention, E", the loss modulus is obtained by the product of E' and tan $\delta$. This affords a reliable, simple, repeatable way of determining the loss modulus of materials. While a particular apparatus that is preferred has been described, it is to be understood that any dynamic resonant apparatus that provides a sine wave drive that is located 90° out of phase with the displacement of the sample can be used.

I claim:

1. A method for determining the loss modulus of a material using a dynamic mechanical system for subjecting said material to a vibratory mechanical displacement comprising the steps of:
   displacing said material a finite distance with a periodic driving force that leads said displacement by about 90°,
   displacing said material said finite distance using a static driving force, thereby to deform said material to the same extent as with said periodic driving force,
   dividing said periodic driving force by said static driving force to obtain the tangent of the loss angle for said material, from which the loss modulus may be calculated.

2. The method of claim 1 wherein said driving force is sinusoidal.

3. The method of claim 2 which includes driving said material with driving forces which are directly related to driving voltages, whereby the quotient of said voltages represents the tangent of the loss angle.

4. In an apparatus for measuring the loss modulus of a material including means for vibrating said material at its resonant frequency using a dynamic mechanical system having a displacement transducer for providing an alternating signal corresponding to the instantaneous displacement of said mechanical system, a drive transducer for imparting mechanical motion to said system, and drive means responsive to said displacement signal for actuating said drive transducer to maintain said mechanical system oscillating at said resonant frequency and at a constant amplitude, said drive means includes analog means for developing an analog signal related in amplitude to the power required to maintain said amplitude constant, and switching means responsive to the zero crossover times of said alternating displacement signal for selectively actuating said drive transducer with said analog signal to maintain said resonant frequency, the improvement comprising:
   means coupled to said switching means for actuating said drive transducer with a sinusoidal signal whose peak value is related in amplitude to said analog signal, whereby the loss function of said material is in phase with said sinusoidal signal.

5. The apparatus of claim 4 wherein said means for actuating said drive transducer includes a sine wave generator connected between said switching means and said drive transducer to provide said sinusoidal signal.

* * * * *

Disclaimer 4,170,141.—*Lecon Woo*, Wilmington, Del. METHOD AND APPARATUS FOR MEASURING THE LOSS MODULUS OF MATERIALS. Patent dated Oct. 9, 1979. Disclaimer filed June 11, 1980, by the assignee, *E. I. du Pont de Nemours and Company*.

Hereby enters this disclaimer to the remaining term of said patent.

[*Official Gazette August 5, 1980.*]